(12) United States Patent
Savage

(10) Patent No.: US 7,268,219 B1
(45) Date of Patent: Sep. 11, 2007

(54) METHOD FOR PRODUCING OR ENHANCING A T-CELL RESPONSE AGAINST A TARGET CELL USING A COMPLEX COMPRISING AN HLA CLASS I MOLECULE AND AN ATTACHING MEANS

(75) Inventor: Philip Michael Savage, Bristol (GB)

(73) Assignee: Alexis Biotech Limited, London (GB)

( * ) Notice: Subject to any disclaimer, the term of this patent is extended or adjusted under 35 U.S.C. 154(b) by 957 days.

(21) Appl. No.: 09/724,985

(22) Filed: Nov. 28, 2000

Related U.S. Application Data

(63) Continuation-in-part of application No. PCT/GB99/01764, filed on Jun. 4, 1999.

(30) Foreign Application Priority Data

Jun. 5, 1998 (GB) .................................. 9812227.8
Apr. 12, 1999 (GB) .................................. 9908333.9

(51) Int. Cl.
C12P 21/08 (2006.01)
C07K 16/18 (2006.01)
C07K 1/10 (2006.01)

(52) U.S. Cl. ................ 530/402; 530/387.3; 530/387.7; 530/388.2; 530/388.22; 530/388.8; 530/391.1; 530/391.5; 530/395; 530/403

(58) Field of Classification Search .................... 514/8; 530/387.3, 387.7, 388.2, 388.22, 388.8, 391.1, 530/391.5, 395; 435/975; 424/134.1, 141.1, 424/143.1, 155.1, 179.1, 192.1, 193.1, 194.1
See application file for complete search history.

(56) References Cited

U.S. PATENT DOCUMENTS 5,026,785 A * 6/1991 Mage et al.
6,548,067 B1 * 4/2003 Seeman et al. .......... 424/192.1

FOREIGN PATENT DOCUMENTS

| EP | 0 352 761 A | 1/1990 |
|---|---|---|
| WO | WO 96/04314 | 2/1996 |
| WO | WO 97/24446 | 7/1997 |
| WO | WO 99/11775 | 3/1999 |
| WO | WO 99/13095 | 3/1999 |
| WO | WO 99/64464 | 12/1999 |

OTHER PUBLICATIONS

Ogg et al. British Journal of Cancer (2000) 82(5):1058-1062.*
Neri, D et al. J. Invest. Dermatol. [1996] 107(2):164-170.*
Huang, J.H. et al., "Protein transfer of performed MHC-peptide complexes sensitizes target cells to T cell cytolysis," *Immunity*, 1(7): 607-13, 1994.
Moris, A. et al., "Cutting Edge: Characterization of Allorestricted and Peptide-Selective Alloreactive T Cells Using HLA-Tetramer Selection", *The Journal of Immunology*, 166: 4818-4821, 2001.
Sadovnikova, E. et al., "Generation of human tumor-reactive cytotoxic T cells against peptides presented by non-self HLA class 1 molecules", *Eur. J. Immunol.*, 28: 193-200, 1998.

* cited by examiner

*Primary Examiner*—Christina Chan
*Assistant Examiner*—F. Pierre VanderVegt
(74) *Attorney, Agent, or Firm*—Frommer Lawrence & Haug LLP; Thomas J. Kowalski; Angela M. Collison

(57) ABSTRACT

A complex comprising an HLA Class 1 molecule and attaching means for selectively attaching the HLA class 1 molecule to a target cell is disclosed, and a method is provided for producing or enhancing an immunological response against a target cell, by attaching said complex to the target cell. Where the target is a diseased, foreign or malignant cell, this method may be used to promote the lysis of the targeted cell by T cells in the immune system. Where the target cell is an antigen presenting cell, this method may be used to promote the proliferation of specific T cell clones. The invention is of potential use in the prevention and treatment of malignant diseases including cancer and leukemia, infectious diseases including viral infections such as HIV, bacterial infections including tuberculosis, and parasitic infections including malaria.

27 Claims, 9 Drawing Sheets

SEQUENCE LISTING

<160> NUMBER OF SEQ ID NOS: 3

<210> SEQ ID NO 1
<211> LENGTH: 8
<212> TYPE: PRT

```
-continued

<213> ORGANISM: Epstein-Barr

<400> SEQUENCE: 1

Arg Ala Lys Phe Phe Gln Leu Leu
1               5

<210> SEQ ID NO 2
<211> LENGTH: 9
<212> TYPE: PRT
<213> ORGANISM: Homo sapiens

<400> SEQUENCE: 2

Ser Leu Tyr Asn Thr Val Ala Thr Leu
1               5

<210> SEQ ID NO 3
<211> LENGTH: 10
<212> TYPE: PRT
<213> ORGANISM: Homo sapiens

<400> SEQUENCE: 3

Glu Ala Ala Gly Ile Gly Ile Leu Thr Val
1               5                   10
```

METHOD FOR PRODUCING OR ENHANCING A T-CELL RESPONSE AGAINST A TARGET CELL USING A COMPLEX COMPRISING AN HLA CLASS I MOLECULE AND AN ATTACHING MEANS

RELATED APPLICATIONS

This application is the continuation-in-part of PCT/GB99/01764, filed Jun. 4, 1999, designating the U.S. and published as WO 99/64464, with claims of priority from Great Britain application Nos. 9812227.8, filed Jun. 5, 1998 and 9908333.9 filed Apr. 12, 1999. All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

This application relates to means for producing or enhancing an immunological response against a target cell, through the attachment of an immunogenic HLA class I molecule thereto. The invention is of potential use in the prevention and treatment of malignant diseases including cancer and leukaemia, infectious diseases including viral infections such as HIV, bacterial infections including tuberculosis, and parasitic infections including malaria.

Cytotoxic T cells in the cellular immune system are responsible for recognising cells that display "foreign" markings, and triggering an immunological response against such cells. Each cytotoxic T cell expresses a number of cell surface recognition receptors, which recognition receptors all possess precise specificity for a particular "foreign" peptide sequence, which recognition receptors are adapted to bind to HLA class I molecules expressed on the surface of cells scanned by the T cell. HLA class I molecules are cell surface molecules which possess a peptide binding groove exposed on the external surface of the cell, which groove is arranged under normal circumstances to bind a peptide derived from the interior of the cell. When a recognition receptor on a cytotoxic T cell recognition receptor is enabled to contact the peptide binding groove of the HLA class I molecule and interact with any peptide contained therein. If this peptide matches the specificity of the recognition receptor, the T cell is said to recognise the scanned cell, and may consequently trigger an immunological response against said scanned cell.

Cytotoxic T cells of various specificities within a host immune system are also able to recognise and trigger an immunological response against a cell exhibiting an HLA class I molecule which is of a different allotype from the HLA class I molecules of the host cells. An immunological response of this kind is known as an "alloreactive" response.

An immunological response against a cell usually results in the lysis of the cell and/or the local release of cytokines. It has however been observed that cytotoxic T cells do not trigger the lysis of so-called antigen presenting cells (APCs) in this way. Instead, the immunological response triggered by T cell recognition of an HLA class I molecule on the surface of an antigen presenting cell results in the direct selective proliferation of the cytotoxic T cell. The host immune system consequently becomes immunised against any cells exhibiting the foreign peptide recognised by the surface recognition receptors on this T cell.

It is recognised that the effector mechanisms of the cellular immune system could be a powerful tool in the prevention and treatment of many illnesses, including malignant processes and infectious and auto-immune diseases, including cancer. A small number of the HLA class I molecules on a tumour cell surface may be found to bind peptides which are selectively expressed or over-expressed in tumour cells and are capable of being recognised by cytotoxic T cells in the immune system. Such peptides may furthermore be tumour specific, being found only infrequently, or not at all, on the HLA class I molecules of non-tumour cells. An example of one such tumour specific peptide is the HMW-MAA antigen found on melanoma cells. However, the number of HLA molecules presenting such peptides is generally too small to stimulate an effective immunological response against the tumour cell. Moreover, such peptides are rarely, if ever, presented by HLA class I molecules on the surface of APCs.

Attempts to enhance the response of the cellular immune system to tumour cells have hitherto focused on increasing tumour cell immunogenicity. In particular, various efforts have been made to produce high-level expression of immunogenic HLA class I molecules on the surface of tumour cells, through the techniques of gene therapy. The delivery of cDNA encoding an HLA class I gene containing an immunogenic peptide in the leader sequence of the HLA molecule has been described in Kang (*Cancer Res.* 57, 1997, 202-205). Meanwhile, Stopeck (*J Clinical Oncology* 5, 1997, 341-349) describes the transfection of allogeneic HLA class I in patients with melanoma. This work has demonstrated some response in clinical trials, but has also highlighted the difficulties involved in targeting turnout cells at multiple sites in vivo through the techniques of gene therapy.

The present application sets out to provide improved means for producing or enhancing an immunological response against a target cell, and to provide an improved method for treating or preventing cancer and other malignant infectious or auto-immune diseases.

Accordingly, in one aspect of the present invention there is provided a complex comprising an HLA class I molecule or fragment thereof, which HLA class I molecule or fragment thereof comprises a T cell binding portion, and attaching means for selectively attaching said HLA class I molecule or fragment thereof to a target cell, characterised in that said HLA class I molecule or fragment thereof binds or is attached to a recognition peptide, which recognition peptide is arranged to be presented by said HLA class I molecule or fragment thereof.

In another aspect of the present invention there is provided a method of attaching an HLA class I molecule or fragment thereof to a target cell, which HLA class I molecule or fragment thereof comprises a T cell binding portion, comprising the step of introducing to said target cell said HLA class I molecule or fragment thereof and attaching means for selectively attaching said HLA class I molecule or fragment thereof to the target cell.

In yet another aspect of the present invention, there is provided a pharmaceutical composition comprising an HLA class I molecule or fragment thereof, which HLA class I molecule or fragment thereof comprises a T cell binding portion; attaching means for selectively attaching said HLA class I molecule or fragment thereof to a target cell; and an appropriate excipient or carrier.

The HLA class I molecule or fragment thereof may bind a peptide, which peptide is arranged to be presented for T cell recognition by said HLA class I molecule or fragment thereof. Said peptide may be attached to the HLA class I molecule or fragment thereof in accordance with the method described in Garboczi (*PNAS* 89, 1992, 3429-3433).

The attaching means preferably comprises a linking polypeptide with high specific affinity for a target cell specific molecule on the surface of the target cell. By "target cell specific molecule" herein is meant any molecule that is characteristically expressed or over-expressed on the surface of the target cell. By way of example, in cancer cells said "target cell specific molecule" could include any of the following tumour associated antigens: carcinoembryonic antigen, placental alkaline phosphatase, polymorphic epithelial mucin, human chorionic gonadotrophin, CD20, prostate specific antigen, ca-125, HMW-MAA and others.

Conveniently, the linking polypeptide will comprise an antibody, preferably a monoclonal antibody, raised against said target cell specific molecule (Riethmuller and Johnson, *Curr. Opin. Immunol.* 4, 1992, 647-655). Suitable antibodies for this purpose include C46, 85A12, H17E2, HMFG1, W14, IF5, 225.28s (Buraggi 1985 *Cancer Res.* 45, 3378-3387), and others. Deposits of the immortalised hybrids producing these antibodies have been made at the American Type Culture Collection, Rockville Md., USA. Further examples of antibodies are described in Maloney et al (*Blood* 84, 1994, 2457-2466), Riethmuller et al (*Lancet* 343, 1994, 1177-1183) and Hird et al (*Br. J. Cancer* 68, 1993, 403-406).

Said linking polypeptide may comprise an antibody raised against a target cell specific molecule and a coupling system for coupling said antibody to said HLA class I molecule or fragment thereof. The coupling system may comprise a two- or three-step chain of well-characterised paired small molecules, joined to the antibody and the HLA class 1 molecule so as to form a stable bridge between the two. Examples of paired small molecules which might be used in this connection include (but are not limited to) biotin and avidin/streptavidin (Moro, 1997 *Cancer Res.* 57, 1922-1928; Altman et al, *Science* 274, 1996, 94-96), and calmodulin and calmodulin binding peptides (Neri, 1996, *J. Invest. Dermatol.* 107, 164-170). Alternatively, said linking polypeptide may comprise an antibody-raised against a target cell specific molecule, which antibody is adapted to be attached directly to said HLA class I molecule or fragment thereof.

In a further possible embodiment of the invention, said complex may comprise a recombinant protein, which recombinant protein includes a moiety comprising said HLA class I molecule or fragment thereof, and a moiety comprising said attaching means.

The HLA class I molecule or fragment thereof may be purified from plasma or platelets or made recombinantly. The HLA class I molecule or fragment thereof may further be arranged to bind and present for T cell recognition a defined peptide of choice, such as a viral, bacterial, parasitic, or tumour-specific peptide. Attachment of the HLA class I molecule or fragment thereof to the target cell may be achieved by introducing said HLA class I molecule or fragment thereof and said attaching means to the vicinity of the target cell. The target cell may be a culture cell in vitro, but will advantageously be in the body of a patient. Preferably, the target cell will be arranged to be contacted by a cytotoxic T cell, which cytotoxic T cell is adapted to recognise said HLA class I molecule or fragment thereof either as being of a mismatched allotype or as binding a foreign peptide, and which cytotoxic T cell is capable of triggering an immunological response against said target cell.

In one embodiment of the present invention the target cell is of a type which may be lysed as a result of an immunological response thereagainst. Advantageously, the target cell is a tumour cell or any diseased or foreign cell the presence of which is undesired in a patient, such as a cancer cell, leukaemia cell, a cell infected with the HIV virus or with any other microbe or virus, a cell responsible for detrimental activity in auto-immune disease, and so on. In order to accelerate the triggering of an immunological response against said target cell in a patient, said HLA class I molecule or fragment thereof will preferably be capable of producing a powerful immune response from the cellular immune system of the patient. Accordingly, said HLA class I molecule or fragment thereof may bind a viral or microbial peptide, preferably a viral or microbial peptide to which the patient is likely to have had previous exposure. In particular, said HLA class I molecule or fragment thereof may bind an influenza virus peptide, a measles virus peptide, an Epstein-Barr virus peptide, in particular an Epstein-Barr virus peptide comprising the RAKFFQLL (SEQ ID NO: 1) epitope of the lytic protein BZLFI, a Cytomegalovirus peptide, or a tetanus toxoid peptide. Alternatively, said HLA class I molecule or fragment thereof may bind any peptide which already has a strong cytotoxic T cell response or which is capable of inducing a powerful immune response. The allotype of said HLA class I molecule or fragment thereof may additionally be different from the allotype of the HLA class I molecules of the patient, so that an alloreactive response may additionally be triggered against said target cell.

In another embodiment of the invention the target cell is an antigen presenting cell (APC). Recognition by a cytotoxic T cell of an HLA class 1 molecule or fragment thereof attached to said APC may result in direct and selective proliferation of the cytotoxic T cell. Accordingly, said HLA class I molecule or fragment thereof will advantageously be adapted to present for T cell recognition a tumour specific peptide as defined above, or a viral peptide, or a bacterial peptide, or a parasitic peptide, or any peptide which is exclusively or characteristically presented by HLA class I molecules on the surface of diseased, malignant or foreign cells the presence of which is undesirable in a patient. Peptides linked to malignant conditions have been characterised (Brossart, 1998 *Cancer Res.* 58, 732-736 and Lucas, 1998 *Cancer Res.* 58, 743-752), as have peptides of parasitic origin (Khusmith, 1991 *Science* 252, 715-718). The attachment of an HLA class I molecule or fragment thereof to an APC, in accordance with the present invention, may be used for in vivo immunisation against cells presenting a given peptide, or ex vivo production of cytotoxic T cells of a particular specificity.

Where the target cell is a tumour cell or microbially infected cell, the pharmaceutical composition of the present invention may be used for the treatment of a tumour or microbial disease respectively, and there is provided a method of treating a tumour or microbial disease in a patient, comprising the step of administering to a patient in need thereof an effective amount of said pharmaceutical composition.

It must be noted that whilst many tumour types express tumour associated antigens, heterogeneity in the level of expression does occur, so some tumour cells may not be targeted by antibody and lysed directly. However, in vitro date from the analogous antibody-superantigen system shows that the high local levels of cytokines released by activated T cells can lead to the death of untargeted bystander tumour cells (Dohlsten et al, *Int. J. Cancer* 54, 1993, 482-488). It is likely that similar effects will occur in a targeting system using MHC class I/peptide complexes. Similarly, it is possible that the presence of activated cytotoxic T cells releasing cytokines in the tumour may lead to enhancement of a specific anti-tumour immune response.

Where the target cell is an APC and the HLA class I molecule or fragment thereof binds a tumour-specific peptide or any peptide which is exclusively or characteristically presented by HLA class I molecules on the surface of a virally, bacterially, parasitically or microbially infected cell, the pharmaceutical composition of the present invention may be used for immunising against the tumour or viral, bacterial, parasitic or microbial infection respectively, and there is provided a method of immunising against a tumour or viral, bacterial, parasitic or microbial infection in a patient, comprising the step of administering to a patient in need thereof an effective amount of said pharmaceutical composition.

The response of said patient may be improved by in vivo cytokine support, or by the infusion of antigen-specific cytotoxic T cells expanded ex vivo. Transient immunosuppression (Ledermann et al, *Int. J. Cancer* 47, 1991, 659-664) may be used to minimise the immunogenic response of a patient to components of the targeting system such as the avidin bridge.

The administration of said pharmaceutical composition may be by way of oral, sublingual, transdermal or parenteral administration.

Said effective amount of the pharmaceutical composition will depend on factors such as the nature and severity of the disorder being treated and on the weight, age and condition of the patient.

For oral or parenteral administration, it is greatly preferred that the pharmaceutical composition is administered in the form of a unit-dose composition, such as a unit dose oral or parenteral composition.

Such compositions are prepared by admixture and are suitably adapted for oral or parenteral administration, and as such may be in the form of tablets, capsules, oral preparations, powders, granules, lozenges, reconstitutable powders, injectable and liquid infusible solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycolate. Suitable lubricants include, for example, magnesium stearate. Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms may be prepared comprising a sterile vehicle. The components of the composition, depending on the vehicle and the concentration, can be either suspended or dissolved. Parenteral solutions are normally prepared by dissolving the components of the composition in a vehicle and filter sterilising before filling into a suitable vial or ampoule and sealing. Advantageously, adjuvants such as a local anaesthetic, preservatives and buffering agents are also dissolved in the vehicle. To enhance the stability, the composition may be frozen after filling into the vial and the water removed under vacuum.

Parenteral suspensions are prepared in substantially the same manner except that the compound may be suspended in the vehicle instead of being dissolved and sterilised by exposure to ethylene oxide before suspending in the sterile vehicle. Advantageously, a surfactant or wetting agent may be included in the composition to facilitate uniform distribution of the compound of the invention.

As is common practice, the compositions will usually be accompanied by written or printed directions for use in the treatment concerned.

Following is a description, by way of example only, and with reference to the accompanying drawings, of methods of putting the present invention into effect.

In the drawings:—

Figure 6:
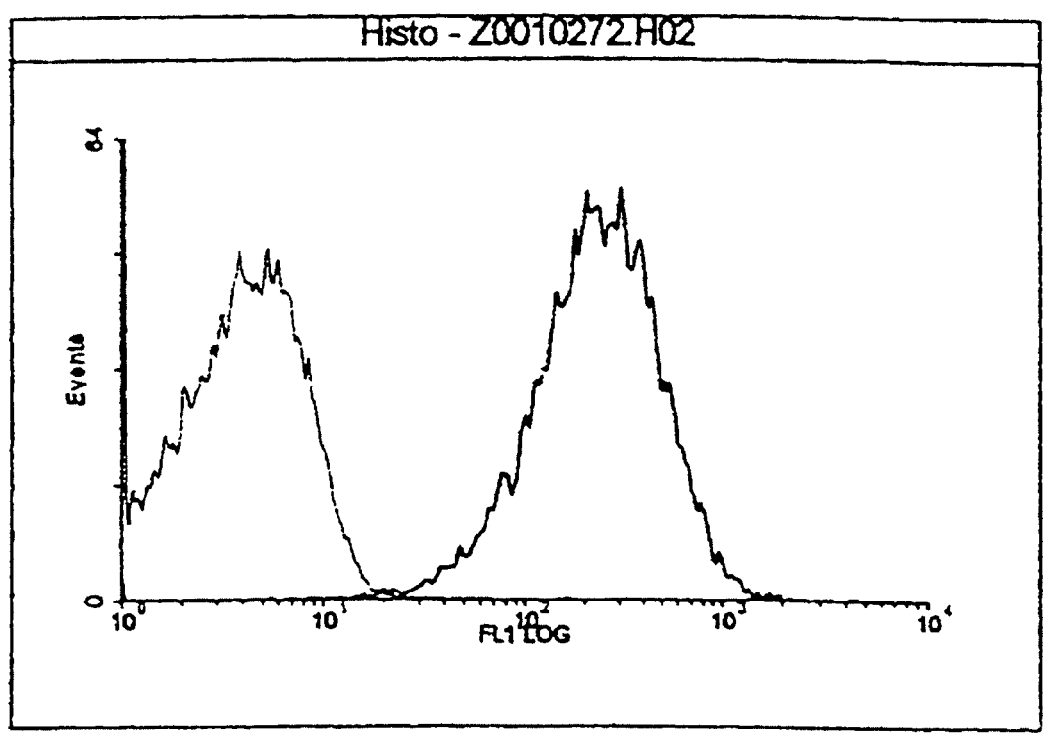

FIG. 6 shows a FACS analysis of HLA-class I deficient Daudi cells targeted with HLA-A2 via biotinylated anti-CD20 mAb. Trace 1 (lefthand trace) corresponds to native untargeted Daudi cells. Trace 2 (righthand trace) corresponds to Daudi cells targeted with mAb/avidin/HLA-A2/gag/FITC anti-MHC class I. Mean fluorescence trace I=0.31, mean fluorescence trace 2=24.3 (arbitrary fluorescence units).

Figure 7:
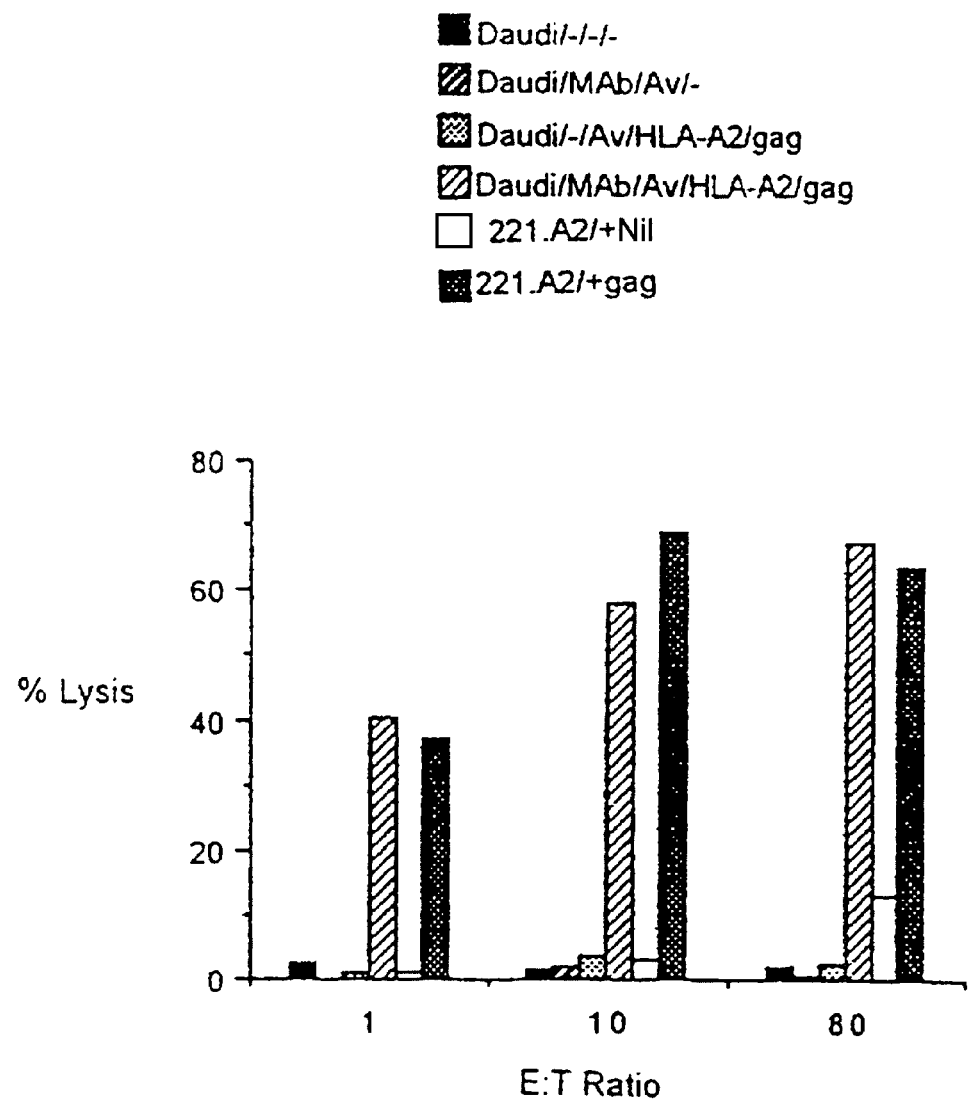

FIG. 7 shows the results of a four hour chromium release assay, described in Example 2 below, in which HLA class I-deficient Daudi cells targeted with various components of the HLA-A2/gag delivery system were incubated with HLA-A2/gag specific cytotoxic T cell clones. A comparison was made with native and peptide-pulsed 221.A2 cells (HLA-A2+ ve).

Figure 8:
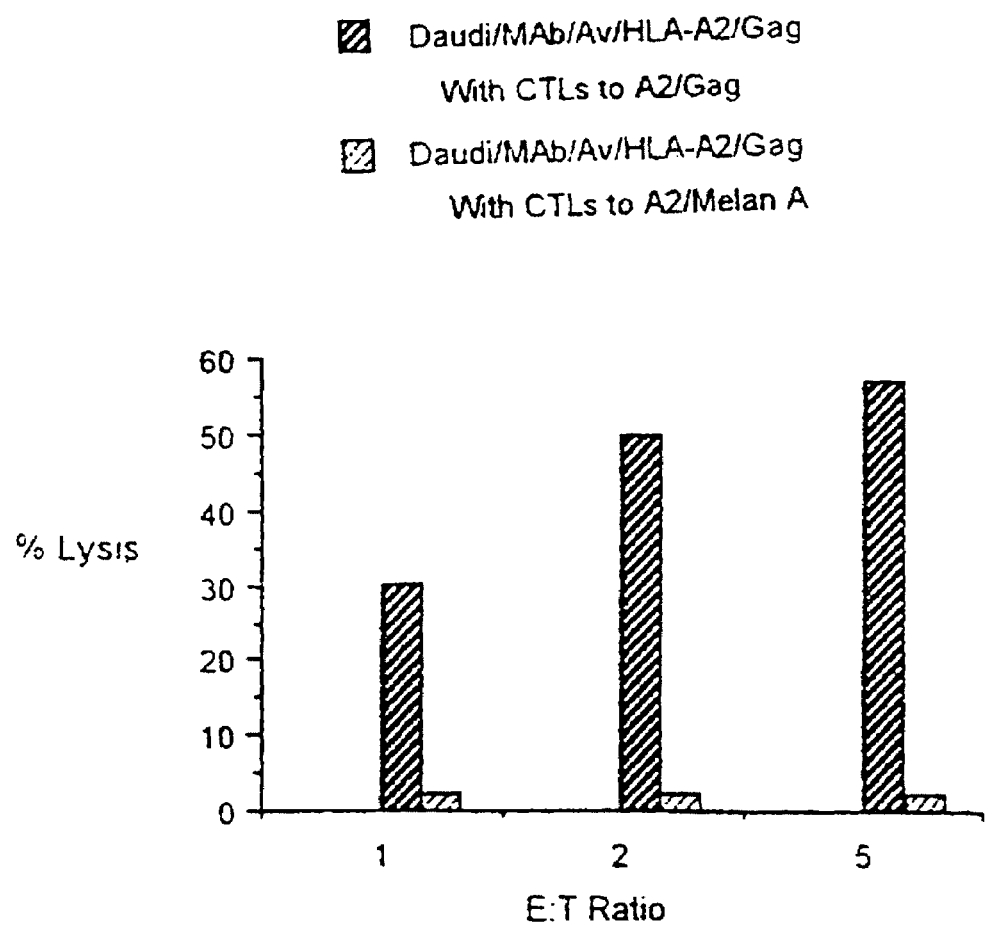

FIG. 8 shows the results of a four hour chromium release assay, described in Example 2 below, in which HLA-A2/gag targeted Daudi cells were incubated with HLA-A2/gag-specific and HLA-A2/Melan A-specific cytotoxic T cell clones.

Figure 9:
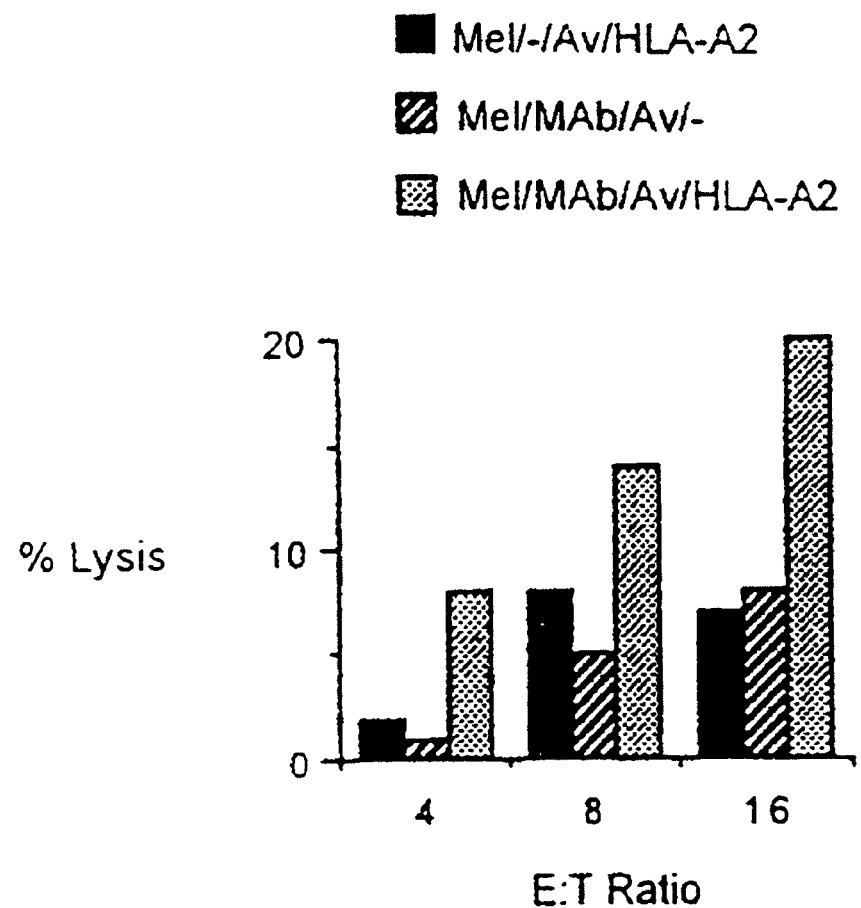

FIG. 9 shows the results of a twenty hour chromium release assay, described in Example 2 below, in which HLA-A2 +ve SK29.Mel cells were incubated with HLA-A2/gag specific cytotoxic T cell clones.

EXAMPLE 1

The following components were used:

| | |
|---|---|
| Target cells: | A human melanoma cell line Mel 1, deposited at the Department of Immunology, Institute of Molecular Medicine, Oxford, that carries the HLA class I allotype HLA-A2. The cell line was grown in standard RPMI tissue culture media. |
| | A human melanoma cell line Mel 2, deposited at the Department of Immunology, Institute of Molecular Medicine, Oxford, that does not carry the HLA class I allotype HLA-A2. The cell line was grown in standard RPMI tissue culture media. |
| Attaching means : | A monoclonal antibody 225.28s (Buraggi 1985 Cancer Res. 45, 3378-3387) that binds to the HMW-MAA antigen on human melanoma cells. Biotin is chemically conjugated onto this antibody as described in Bayer 1990, Methods Embryology 184, 138-160. |
| | Pure hen egg avidin obtained commercially from Societa Prodotti Antibiotici, Milan, Italy. |
| HLA: | Biotin conjugated recombinant HLA class I allotype HLA-A2 molecules, as described in Altman 1996, Science 274, 94-96, further containing the "gag" peptide that is part of the HIV virus. This peptide comprises the amino acid sequence -SLYNTVATL-. Methods for the preparation/isolation thereof are described in Johnson 1991, J Immunol 147, 1512. The "gag" peptide was attached to the HLA-A2 molecules as described in Garboczi 1992, PNAS 89, 3429-3433. |
| T cells: | HLA-A2/gag specific cytotoxic T cells obtained from an A2+ve HIV patient as described in Altman 1994, Science 274, 94-96. |

In order to establish the ability of the attaching means to cause display of the HLA class I molecules on the surface of Mel 2 target cells, approximately 200,000 cells were first incubated with biotin conjugated monoclonal antibody 225.28s at a final concentration of 20 μg/ml at 37° C. for 30 minutes. Following this the cells were washed in tissue culture media (RPMI 1640, obtainable from Gibco, Scotland). The Mel 2 cells were then incubated with avidin at a final concentration of 10 μg/ml for 10 minutes at 37° C. and washed in tissue culture media. Finally, the Mel 2 cells were incubated with biotin conjugated HLA class I HLA-A2/gag molecules at a final concentration of 20 μg/ml at 37° C. for 20 minutes.

Figure 1:
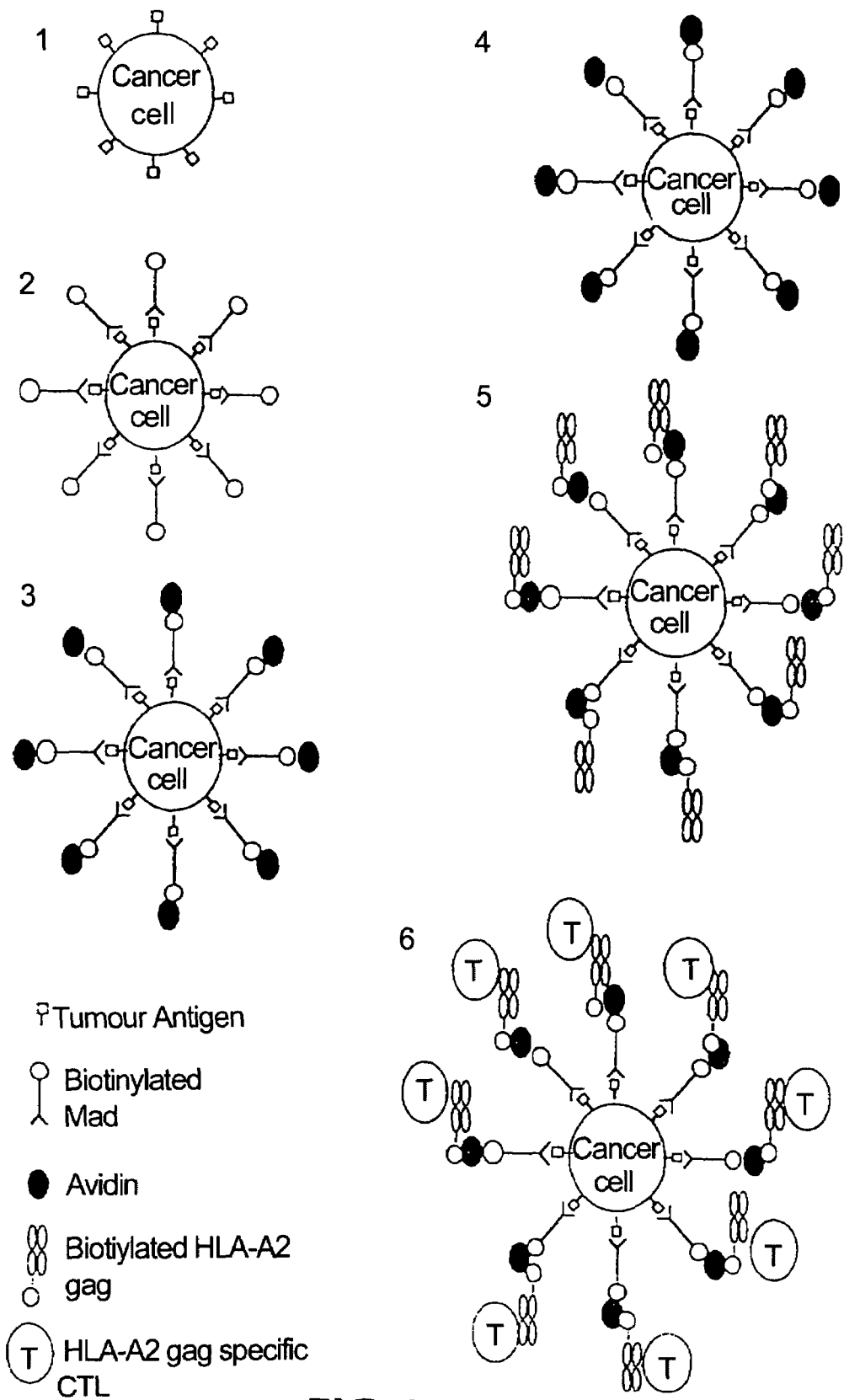
FIG. 1 shows a diagram showing the method/idea for delivering HLA molecules to the surface of tumour cells.
Figure 2:
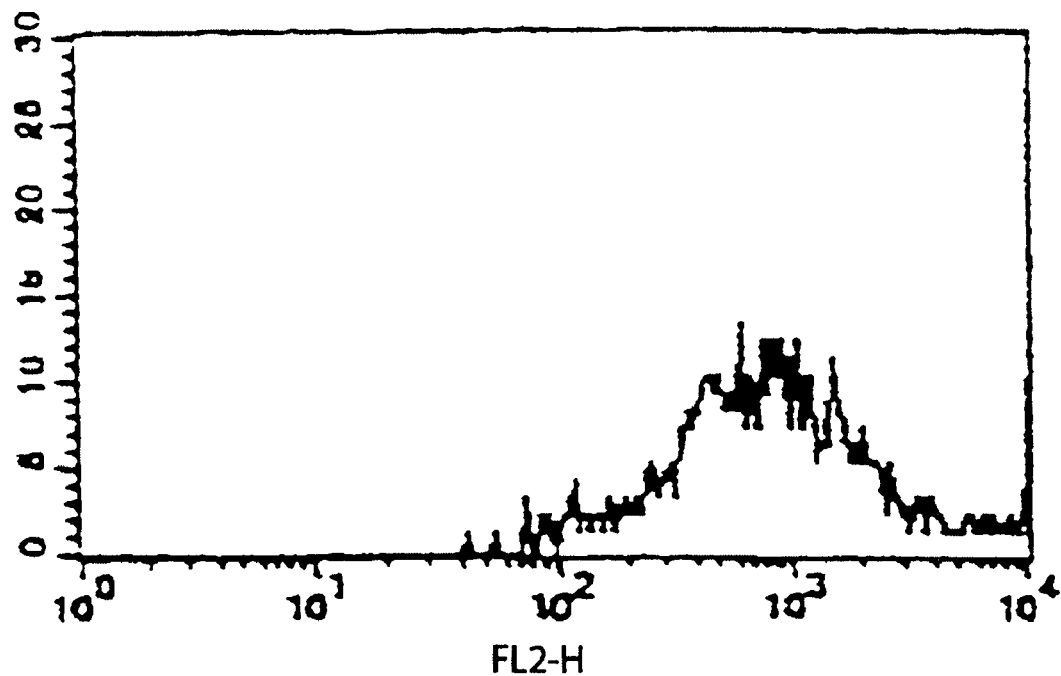
FIG. 2 shows a FACs analysis of HLA-A2-ve Mel 2 melanoma cells treated with biotin-conjugated monoclonal antibody 225.28s, avidin, biotin-conjugated HLA-A2/gag complexes, anti-HLA-A2 monoclonal antibody BB7.2 and phycoerythrin-conjugated rabbit anti-mouse antibody.

The binding of recombinant HLA-A2 to the treated Mel 2 cells was shown by the attachment of anti-HLA-A2 monoclonal antibody BB7.2 (Santos-Aguado 1988, *J. Immunol* 141, 2811-2818) following incubation with BB7.2 antibody at a final concentration of 10 μg/ml at 37° C. for 30 minutes. After washing in tissue culture media the cells were incubated with phycoerythrin conjugated rabbit anti-mouse antibody (Sigma, Poole, UK) at a final concentration of 10 μg/ml for 30 minutes at 37° C. and analysed in a Becton Dickson Facscan machine. The result of this analysis is shown in FIG. 2 which demonstrates a positive signal indicating the presence of HLA-A2 molecules attached to the surface of the Mel 2 cells.

A chromium release T cell cytotoxicity assay was then performed in order to establish the ability of HLA-A2/gag specific T cell clones to lyse Mel 1 cells coated with HLA-A2/gag in accordance with the present method. Approximately $10^6$ Mel 1 cells were first pre-incubated with 1.85 μBq $Na_2^{51}CrO_4$ (obtained from Amersham International, Amersham, UK) for 1 hour at 37° C. The pre-incubated Mel 1 cells were then incubated with biotin conjugated monoclonal antibody 225.28s at a final concentration of 20 μg/ml at 37° C. for 30 minutes, and washed in tissue culture media. Following this, the Mel 1 cells were incubated with avidin at a final concentration of 10 μg/ml for 10 minutes at 37° C. and then washed again in tissue culture media. The Mel 1 cells were then incubated with biotin conjugated HLA class I HLA-A2/gag molecules at a final concentration of 20 μg/ml at 37° C. for 20 minutes and washed with tissue culture media.

Having been coated with HLA class I HLA-A2/gag, the chromium-treated Mel 1 cells were then incubated with HLA-A2/gag specific cytotoxic T cells in ratios of 0:1 to 20:1 of effector to target cells at 37° C. for 20 hours. Lysis of Mel 1 cells treated with $Na_2^{51}CrO_4$ results in the release of radioactive chromium, which may be detected by analysis in a scintillation counter. In order to establish the percentage of Mel 1 cells lysed following incubation with HLA-A2/gag specific cytotoxic T cells, the following measurements were taken: background release of chromium from the Mel 1 cells in media alone ("M"); release of chromium from the Mel 1 cells following incubation with the T cells ("E"); (release of chromium from the Mel 1 cells following final treatment with 5% Triton X-100 detergent ("T"). Treatment with detergent will cause the lysis of all the remaining intact Mel 1 cells.

% Mel 1 lysis by cytotoxic T cells was calculated as follows:

$$\% \ lysis = 100 \times \frac{(E - M)}{(T - M)}$$

This analysis was carried out on Mel 1 cells treated with biotin-conjugated 225.28s, avidin, and biotin-conjugated HLA-A2/gag. As a control, the analysis was also carried out on Mel 1 cells treated with biotin-conjugated 225.28s and avidin alone, and on Mel 1 cells treated with avidin and biotin-conjugated HLA-A2/gag alone.

Figure 3:
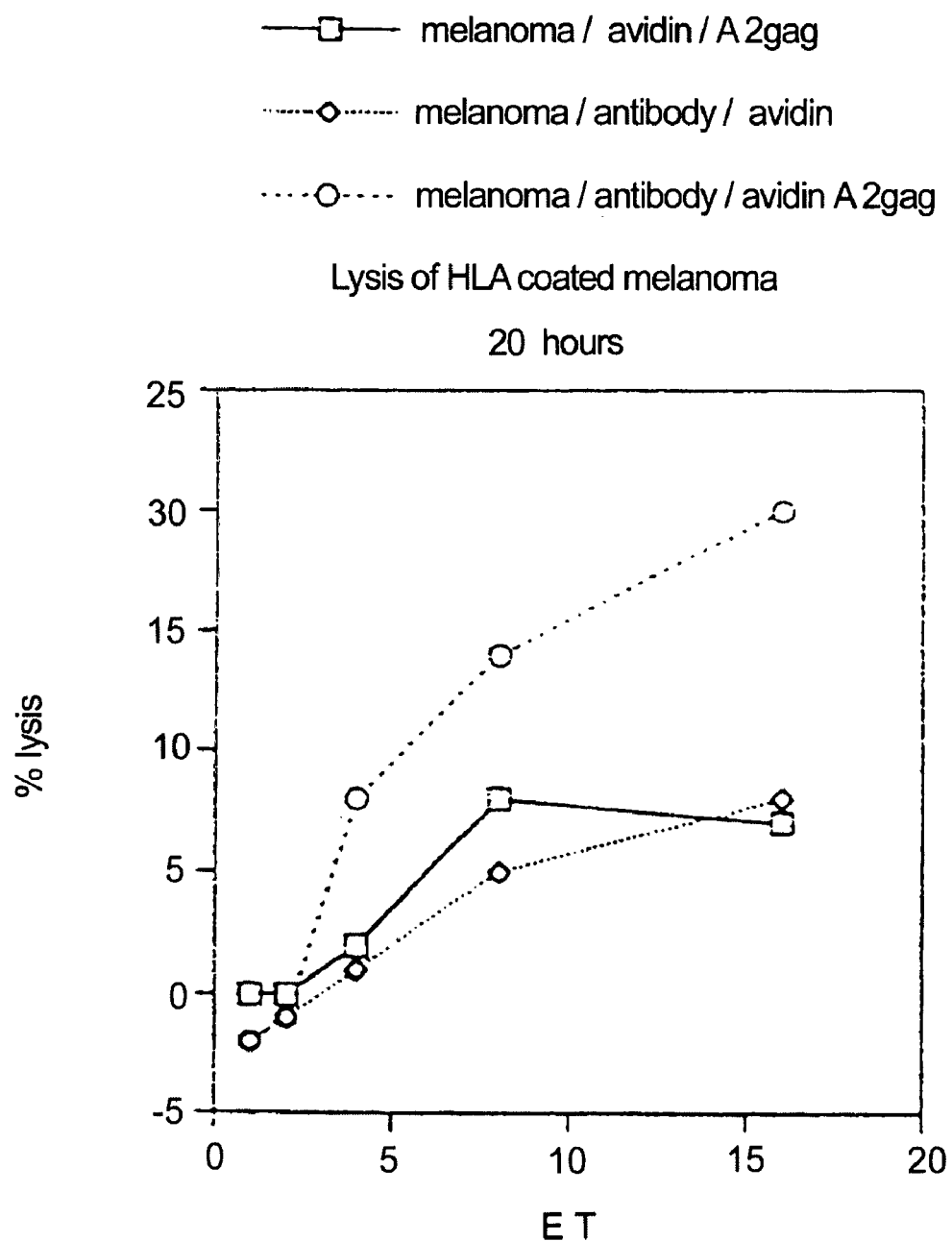
FIG. 3 shows the results of a T cell cytotoxicity chromium release assay with Mel 1 cells treated with the delivery system of biotin-conjugated monoclonal antibody 225.28s, avidin, and biotin-conjugated HLA-A2/gag complexes. These cells were incubated with HLA-A2/gag specific cytotoxic T cells with effector/target ratios of 0:1-20:1 for 20 hours.
Figure 4:
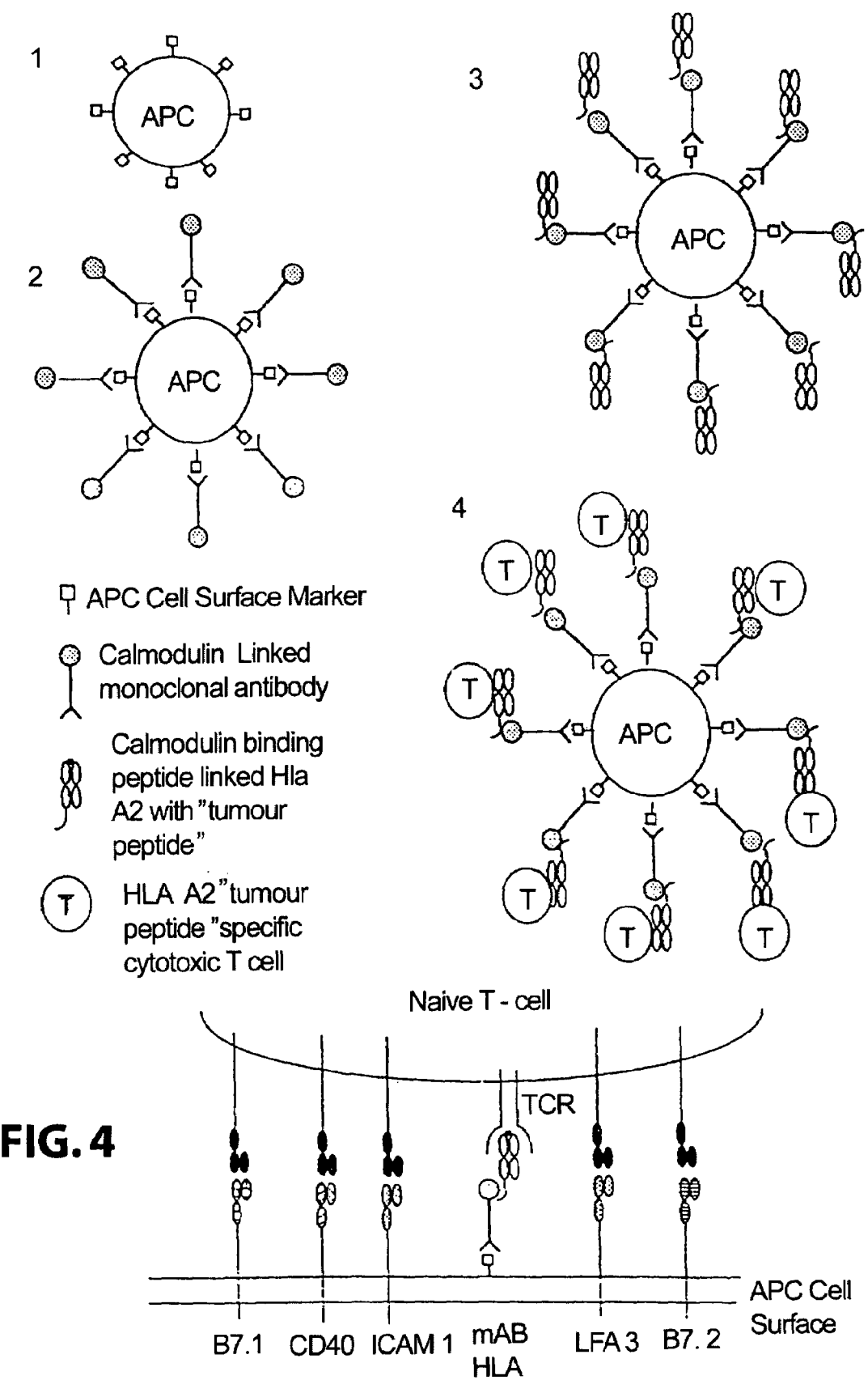
FIG. 4 shows a diagram showing the method/idea for delivering HLA class I/peptide complexes to antigen presenting cells.

The key results of this analysis are illustrated in FIG. 3, which indicates that significant lysis (20%) of Mel 1 cells by HLA-A2/gag specific cytotoxic T cells occurs only when the Mel 1 cells have been treated with all the components of the attaching and delivery means of the present invention (i.e. biotin-conjugated 225.28s monoclonal antibodies, avidin, and biotin-conjugated HLA-A2/gag). No significant increase in cell lysis over background levels was observed in either of the control runs.

EXAMPLE 2

The following components were used:

| | |
|---|---|
| Target cells: | The Daudi B cell line (MHC class I-negative) melanoma line SK-mel-29 (HLA-A2.1-positive), .221/A2 (HLA-A2.1-positive), were maintained in RPMI media with 10% fetal calf serum and antibiotics in a 37° C. incubator with 5% $CO_2$. |
| Attaching means: | Monoclonal antibodies 225.28s (Buraggi 1985 Cancer Res. 45, 3378-3387) and 2H7 that bind to the HMW-MAA antigen. Biotin is chemically conjugated onto these antibodies as described in Bayer 1990, Methods Embryology 184, 138-160. |
| | Pure hen egg avidin obtained commercially from Societa Prodotti Antibiorici, Milan, Italy. |

| | |
|---|---|
| -continued | |
| HLA: | Biotinylated complexes of recombinant MHC class I and peptide were produced as described previously (Altman et al, Science 274, 1996, 94-96; Ogg et al, Science 279, 1998, 2103). Prokaryotic expression of B2M and MHC class I heavy chain, modified by the C terminal addition of a target sequence for the biotin ligase enzyme BirA, was followed by inclusion body purification. Following refolding of heavy chain and B2M around specific peptide, complexes of 45 kD were isolated by gel filtration, biotinylated overnight using BirA in the presence of ATP, Mg2+ and biotin, and then purified by gel filtration and anion exchange. |
| T cells: | Human cytotoxic T cell clones 010 (specific for HLA-A2/gag 77-85 = SLYNTVATL (SEQ ID NO:2) (Parker et al, J Immunol. 149. 1992, 3580-3587)) and IF9 (specific for HLA-A2/melan-A 26-35 = EAAGIGILTV (SEQ ID NO:3) (Romero et al, J. Immunol. 159, 1997, 2366) were maintained in media supplemented with 5% human serum and IL-2 100 IU/ml. |

The stability of the MHC class I/peptide complexes was first established by an ELISA assay. Various MHC class I/peptide complexes, including HLA-A2/Gag3Y, HLA-A2/Gag3F, HLAA2/Lmp2, HLA-B35/Env and HLA-B35/nef, were prepared as outlined above, and were pre-incubated at 10 ug/mil in tissue culture media for 0-20 hours at 37° C. ELISA plates were coated with the mAb W6/32 (5 ug/ml in carbonate buffer pH 9.6 overnight at 4° C.) which recognises conformationally correct MHC class I molecules (Parham, 1979), and then blocked by incubation in 1% bovine serum albumin for 2 hours at 37° C. The MHC class I/peptide complexes were incubated for 30 minutes with the ELISA plates at room temperature, and binding was detected with rabbit anti-human B2 microglobulin followed by alkaline phosphatase conjugated goat anti-rabbit immunoglobulin, and substrate. All incubations were separated by extensive washes in PBS.

Absorbances at 600 nm were measured in a Titertek Multiscan ELISA reader. Three assays were performed for each sample, and the mean reading was calculated.

Figure 5:
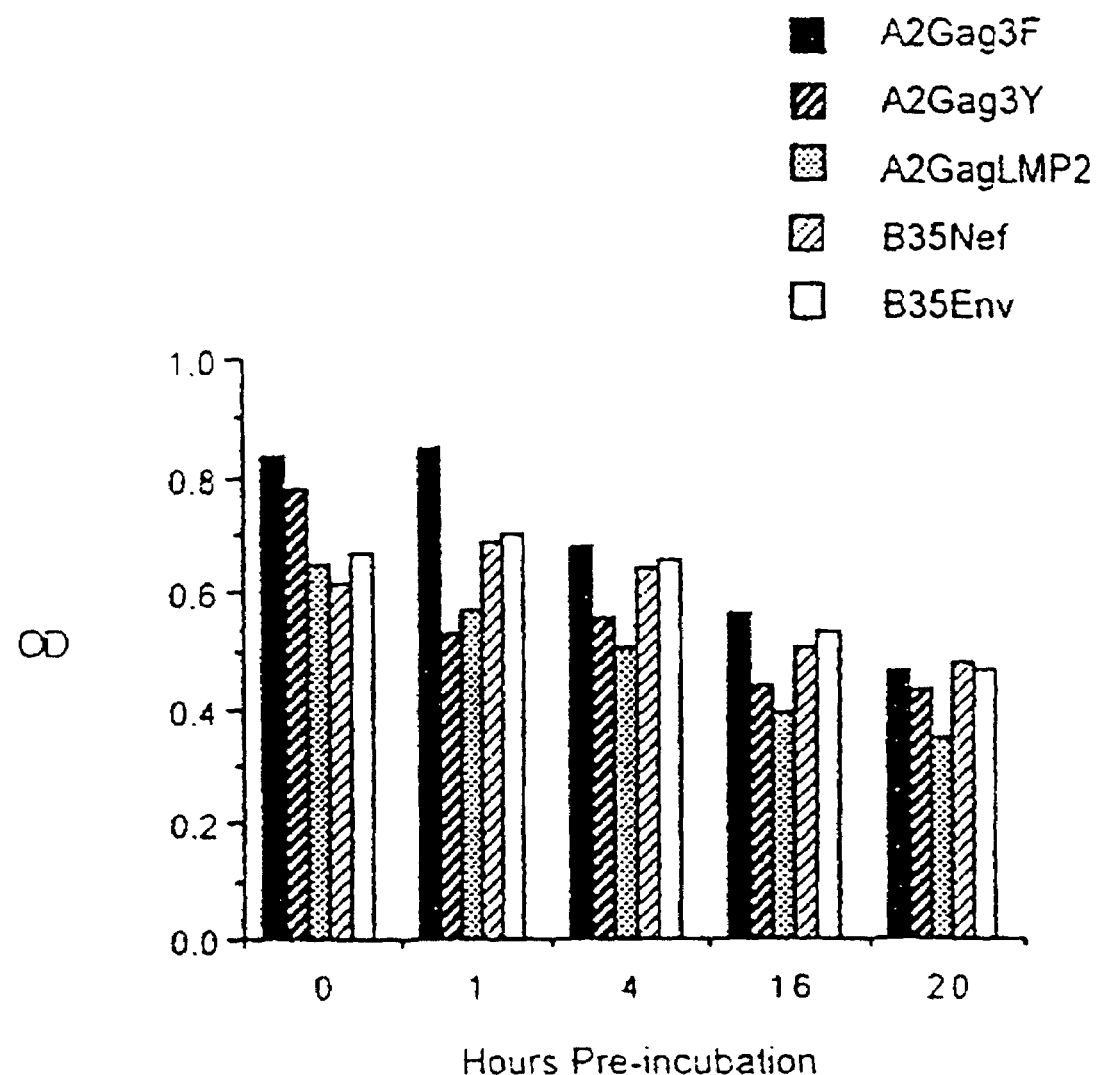
FIG. 5 shows the results of an ELISA assay, described in Example 2 below, for demonstrating the stability of various MHC class I/peptide complexes at 37° C. The results shown are the mean of assays performed on each sample in triplicate.

The results obtained with samples preincubated for 0, 1, 4, 16 and 20 hours are shown in FIG. 5. The results demonstrate that the HLA-A2/gag complexes have appreciable stability in culture media at 37° C., with an estimated half-life in excess of 24 hours.

In storage at 0.5-1 mg/ml at 4° C. HLA-A2/gag complexes appear to be stable for at least 12 months (data not shown).

To demonstrate the ability of the attaching means to cause display of MHC class I on the surface of Daudi cells, Daudi cells deficient in MHC class I were sequentially incubated at 4° C. with biotinylated anti-CD20 (Ancell, Nottingham, UK; mAb 2H7 (Berenson et al, Blood 67, 1986, 509-515) at 1 ug/ml for 30 minutes); hen egg avidin (S.P.A., Milan, Italy, at 10 ug/ml for 10 minutes); biotinylated HLA-A2/gag (at 10 ug/ml for 10 minutes); and FITC labelled anti-MHC class I (Ancell, Nottingham, UK; mAB 3F10 (Eisenbarth et al, J. Immunol. 124, 1980, 1237-1244) at 10 ug/ml). Parallel controls omitted one or other incubation. Cells were washed 3 times in PBS between stages and then fixed in PBS plus 2% formaldehyde and analysed by flow cytometry.

Cells incubated with all three layers of the labelling system had high levels of detectable MHC class I/peptide on their surface compared to untreated Daudi cells (FIG. 6). Cells treated with only any 2 components of the 3-step system gave fluorescence levels comparable to untreated cells (data not shown).

A chromium release cytotoxicity assay was carried out to establish the ability of specific T cell clones to lyse Daudi or SK-mel-29 cells in accordance with the present invention. Daudi or SK-mel-29 cells were incubated with $^{51}CrO_4$ at 2 uCi/uL for 1 hour at 37° C. and then sequentially incubated with: the biotinylated mAbs 2H7 or 225.28s (anti-HMW-MAA) respectively; avidin; and biotinylated HLA-A2/gag complexes as detailed above. Peptide pulsed target cells were incubated with gag 77-85 or melan-A 26-35 peptides at 0.1 uM for 1 hour at 37° C. After washing, labelled target cells were plated into 96-well round bottom plates at 2,500 cells per well, followed by human CTLs at various effector:target ratios. Following incubation at 37° C., 20 ul of supernatant was collected and the amount of $^{51}Cr$ released was determined. The percentage of cytotoxicity (lysis) obtained at each effector:target ratio was calculated as: $100\times(E-M)/(T-M)$, where E=Experimental release, M=Release in media and T=Release in 5% Triton X-100 detergent.

The results shown in FIG. 7 are the mean of experiments performed in duplicate. As shown by these results, the CTL clone (010) efficiently lysed HLA-A2-positive targets (0.221/A2) only when these were pre-incubated with the HLA-A2/gag peptide. MHC class I-negative Daudi cells, when targeted with the HLA-A2/gag complexes of the present invention, were recognised and lysed by this CTL clone to an equivalent degree Untargeted Daudi cells and cells targeted with only 2 of the 3 components of the targeting system were not recognised (maximal lysis <4% at E:T ratios of up to 80:1).

Control CTL, showing a different HLA7A2-restricted specificity (HLA—A2/melan-A), did not lyse Daudi cells targeted with the HLA-A2/gag complexes (FIG. 8), demonstrating the fine specificity of the targeting approach.

Untreated Daudi cells pulsed with gag peptide alone were not lysed by clone 010 (data not shown), in keeping with their lack of endogenous MHC class I.

The ability of antibody-directed HLA-A2/gag complexes to sensitise the melanoma cell line SK-mel-29 to lysis by HLA-A2/gag-specific CTL line is shown in FIG. 8. At all E:T ratios, melanoma cells targeted by complexes linked to surface proteins were lysed substantially more than controls exposed to only two components of the 3-step targeting system. Additionally, MM9 melanoma cells that do not express HLA-A2 were also lysed in a similar manner (data not shown).

The invention claimed is:

1. A complex comprising an HLA class I molecule or fragment thereof having a peptide binding groove, the HLA class I molecule or fragment thereof comprising a T cell recognition portion, and an attachment means for selectively attaching said HLA class I molecule or fragment thereof to a target cell, wherein the HLA class I molecule or fragment thereof is bound or is attached to a recognition peptide in the peptide binding groove of the HLA class I molecule or fragment thereof, wherein the recognition peptide is arranged to be presented by said HLA class I molecule or fragment thereof for T cell recognition, wherein the attachment means comprises:
 a) a linking polypeptide with specific affinity for a molecule on the surface of the target cell; and
 b) a coupling system for coupling the linking polypeptide to the HLA class I molecule or fragment thereof, wherein the coupling system comprises:
  (i) a first small molecule joined to the linking polypeptide; and
  (ii) a second small molecule joined to the HLA class I molecule,
wherein the first and second small molecules are each selected from biotin and avidin/streptavidin or calmodulin and calmodulin binding peptides;
wherein interaction of the small molecules forms a stable bridge between the linking polypeptide and the HLA class I molecule.

2. The complex as claimed in claim 1, wherein said linking polypeptide comprises an antibody raised against said molecule on the surface of the target cell.

3. The complex as claimed in claim 2, wherein the antibody is a monoclonal antibody.

4. The complex as claimed in claim 1, which complex comprises:
 (i) a moiety comprising a recombinant protein that includes said HLA class I molecule or fragment thereof, and
 (ii) a moiety comprising said attachment means.

5. The complex as claimed in claim 1, wherein the recognition peptide comprises a peptide which has a cytotoxic T cell response or which is capable of inducing an immune response.

6. The complex as claimed in claim 1, wherein said recognition peptide comprises one or more of a tumour specific peptide, a viral peptide, a bacterial peptide, a parasitic peptide or microbial peptide.

7. The complex as claimed in claim 1, wherein the allotype of said HLA class I molecule or fragment thereof is different from the allotype of the HLA class I molecules of a subject, so that an alloreactive response can additionally or alternatively be triggered against said target cell.

8. A complex as claimed in claim 1, wherein the recognition peptide comprises a tumour specific peptide, or a viral peptide, or a bacterial peptide, or a parasite peptide, or any peptide which is presented by HLA class I molecules on the surface of diseased or malignant cells, or virally, bacterially, parasitically or microbially infected cells, or foreign cells.

9. The complex as claimed in claim 1, wherein said target cell is a culture cell.

10. A method of preparing a composition comprising a target cell, a complex as claimed in claim 1 and an appropriate excipient or carrier comprising providing a target cell, selectively attaching the complex of claim 1 to the target cell, and addition of said excipient or carrier.

11. A composition comprising a complex as claimed in claim 1 and an appropriate excipient or carrier.

12. The complex of claim 1 wherein the target cell is a B cell.

13. A pack or kit comprising one or more containers, each container having therein a composition as claimed in claim 11, and written instructions for the use of said composition.

14. A complex comprising an HLA class I molecule or fragment thereof having a peptide binding groove, the HLA class I molecule or fragment thereof comprising a T cell recognition portion, and an attachment means for selectively attaching said HLA class I molecule or fragment thereof to a target cell, wherein the HLA class I molecule or fragment thereof is bound or is attached to a recognition peptide in the peptide binding groove of the HLA class I molecule or fragment thereof, wherein the recognition peptide is arranged to be presented by said HLA class I molecule or fragment thereof for T cell recognition, wherein the attachment means comprises:
  a) a linking polypeptide with specific affinity for a molecule on the surface of the target cell; and
  b) a coupling system for coupling the linking polypeptide to the HLA class I molecule or fragment thereof, wherein the coupling system consists essentially of:
    (i) a first small molecule joined to the linking polypeptide; and
    (ii) a second small molecule joined to the HLA class I molecule,
  wherein the first and second small molecules are each selected from biotin and avidin/streptavidin or calmodulin and calmodulin binding peptides;
  wherein interaction of the small molecules forms a stable bridge between the linking polypeptide and the HLA class I molecule.

15. The complex as claimed in claim 14, wherein said linking polypeptide comprises an antibody raised against said molecule on the surface of the target cell.

16. The complex as claimed in claim 15, wherein the antibody is a monoclonal antibody.

17. The complex as claimed in claim 14, which complex comprises:
  a moiety comprising a recombinant protein that include said HLA class I molecule or fragment thereof,
  (ii) and a moiety comprising said attachment means.

18. The complex as claimed in claim 14, wherein the recognition peptide comprises a peptide which has a cytotoxic T cell response or which is capable of inducing an immune response.

19. The complex as claimed in claim 14, wherein said recognition peptide comprises one or more of a tumour specific peptide, a viral peptide, a bacterial peptide, a parasitic peptide or microbial peptide.

20. The complex as claimed in claim 14, wherein the allotype of said HLA class I molecule or fragment thereof is different from the allotype of the HLA class I molecules of a subject, so that an alloreactive response can additionally or alternatively be triggered against said target cell.

21. The complex as claimed in claim 14, wherein said target cell is a culture cell.

22. A composition comprising a complex as claimed in claim 14 and an appropriate excipient or carrier.

23. A pack or kit comprising one or more containers, each container having therein a composition as claimed in claim 22, and written instructions for the use of said composition.

24. A method of preparing a composition comprising target cell, a complex as claimed in claim 14 and an appropriate excipient or carrier comprising providing a target cell, selectively attaching the complex of claim 14 to the target cell, and addition of said excipient or carrier.

25. A complex comprising an HLA class I molecule or fragment thereof having a peptide binding groove, the HLA class I molecule or fragment thereof comprising a T cell recognition portion, and an attachment means for selectively attaching said HLA class I molecule or fragment thereof to a target cell, wherein said attachment means comprises a linking polypeptide which is bound or is attached to said target cell and wherein said linking polypeptide is attached directly to said HLA class I molecule or fragment thereof; and wherein the HLA class I molecule or fragment thereof additionally is bound or is attached to a recognition peptide in the peptide binding groove of the HLA class I molecule or fragment thereof, wherein the recognition peptide is arranged to be presented by said HLA class I molecule or fragment thereof for T cell recognition.

26. A complex comprising an HLA class I molecule or fragment thereof having a peptide binding groove, the HLA class I molecule or fragment thereof comprising a T cell recognition portion, and an attachment means for selectively attaching said HLA class I molecule or fragment thereof to a target cell, wherein the HLA class I molecule or fragment thereof is bound or is attached to a recognition peptide in the peptide binding groove of the HLA class I molecule or fragment thereof, wherein the recognition peptide is arranged to be presented by said HLA class I molecule or fragment thereof for T cell recognition, wherein the attachment means comprises:
  a) a linking polypeptide with specific affinity for a molecule on the surface of the target cell; and
  b) a coupling system for coupling the linking polypeptide to the HLA class I molecule or fragment thereof, wherein the coupling system consists essentially of:
    (i) a first small molecule joined to the linking polypeptide; and
    (ii) a second small molecule joined to the HLA class I molecule,
  wherein interaction of the small molecules forms a stable bridge between the linking polypeptide and the HLA class I molecule and wherein said coupling system consists of biotin and avidin/streptavidin.

27. A complex comprising an HLA class I molecule or fragment thereof having a peptide binding groove, the HLA class I molecule or fragment thereof comprising a T cell recognition portion, and an attachment means for selectively attaching said HLA class I molecule or fragment thereof to a target cell, wherein the HLA class I molecule or fragment thereof is bound or is attached to a recognition peptide in the peptide binding groove of the HLA class I molecule or fragment thereof, wherein the recognition peptide is arranged to be presented by said HLA class I molecule or fragment thereof for T cell recognition, wherein the attachment means comprises:
  a.) a linking polypeptide with specific affinity for a molecule on the surface of the target cell; and
  b.) a coupling system for coupling the linking polypeptide to the HLA class I molecule or fragment thereof, wherein the coupling system consists essentially of:
    (i) a first small molecule joined to the linking polypeptide; and
    (ii) a second small molecule joined to the HLA class I molecule,
  wherein interaction of the small molecules forms a stable bridge between the linking polypeptide and the HLA class I molecule and wherein said coupling system consists of calmodulin and calmodulin binding peptide.

* * * * *

UNITED STATES PATENT AND TRADEMARK OFFICE
CERTIFICATE OF CORRECTION

PATENT NO. : 7,268,219 B1
APPLICATION NO. : 09/724985
DATED : September 11, 2007
INVENTOR(S) : Savage It is certified that error appears in the above-identified patent and that said Letters Patent is hereby corrected as shown below:

Column 13, Claim 17, Line 27 should read

17. The complex as claimed in claim 14, which complex comprises:
(i) a moiety comprising a recombinant protein that ~~include~~includes said HLA class I molecule or fragment thereof,
(ii) and a moiety comprising said attachment means.

Column 13, Claim 24, Line 52 should read

24. A method of preparing a composition comprising a target cell, a complex as claimed in claim 14 and an appropriate excipient or carrier comprising providing a target cell, selectively attaching the complex of claim 14 to the target cell, and addition of said excipient or carrier.

Signed and Sealed this

Twenty-seventh Day of November, 2007

JON W. DUDAS
*Director of the United States Patent and Trademark Office*